(12) United States Patent
Buckley et al.

(10) Patent No.: US 8,276,585 B2
(45) Date of Patent: Oct. 2, 2012

(54) SYSTEMS AND METHODS FOR VISUALIZING PRESSURES AND PRESSURE RESPONSES TO SLEEP-RELATED TRIGGERING EVENTS

(75) Inventors: Mark David Buckley, Buchendorf (DE); Glenn Richards, Clevedon (NZ)

(73) Assignee: ResMed Limited (AU)

( * ) Notice: Subject to any disclaimer, the term of this patent is extended or adjusted under 35 U.S.C. 154(b) by 1321 days.

(21) Appl. No.: 11/998,852

(22) Filed: Nov. 30, 2007

(65) Prior Publication Data

US 2008/0251078 A1 Oct. 16, 2008

Related U.S. Application Data

(60) Provisional application No. 60/907,589, filed on Apr. 10, 2007.

(51) Int. Cl.
*A61M 16/00* (2006.01)
(52) U.S. Cl. ......... 128/204.23; 128/200.24; 128/204.18; 128/204.21
(58) Field of Classification Search ............. 128/200.24, 128/204.18, 204.21, 204.23, 205.25, 206.21, 128/207.13
See application file for complete search history.

(56) References Cited

U.S. PATENT DOCUMENTS

| | | | |
|---|---|---|---|
| 5,097,424 A * | 3/1992 | Ginevri et al. ........... | 128/204.23 |
| 5,245,995 A | 9/1993 | Sullivan et al. | |
| 5,458,137 A * | 10/1995 | Axe et al. .................. | 128/204.23 |
| 6,085,747 A * | 7/2000 | Axe et al. .................. | 128/204.23 |
| 6,349,724 B1 * | 2/2002 | Burton et al. ............. | 128/204.18 |
| 6,360,745 B1 * | 3/2002 | Wallace et al. ........... | 128/204.21 |
| 6,398,739 B1 | 6/2002 | Sullivan et al. | |
| 6,635,021 B1 | 10/2003 | Sullivan et al. | |
| 6,770,037 B2 | 8/2004 | Sullivan et al. | |
| 7,004,908 B2 | 2/2006 | Sullivan et al. | |
| 7,141,021 B2 | 11/2006 | Sullivan et al. | |
| 2001/0035186 A1 * | 11/2001 | Hill ........................... | 128/204.18 |

\* cited by examiner

*Primary Examiner* — Annette Dixon
(74) *Attorney, Agent, or Firm* — Lerner, David, Littenberg, Krumholz & Mentlik, LLP

(57) ABSTRACT

Systems and methods for visualizing patient treatment data collected while a patient suffering from sleep-disordered breathing is treated are provided. For example, according to certain example embodiments, a PAP device for treating a patient suffering from sleep-disordered breathing is provided. A processor may be set or programmed to generate a signal indicative of a triggering event. A flow generator may be configured to provide a supply of pressurized breathable gas to the patient based at least in part on the signal. Recording programmed logic circuitry may be provided to record in a data log pressures provided during patient treatment and triggering events occurring during patient treatment. Visualizing programmed logic circuitry in communication with the PAP device may be configured to read the data log and generate a visual depiction of provided pressures over time. Triggering events may include, for example, one or more of apnea, hypopnea, flattening, snore, etc.

39 Claims, 5 Drawing Sheets

SYSTEMS AND METHODS FOR VISUALIZING PRESSURES AND PRESSURE RESPONSES TO SLEEP-RELATED TRIGGERING EVENTS

CROSS-REFERENCES TO RELATED APPLICATIONS

This application claims the benefit of the filing date of U.S. Provisional Patent Application No. 60/907,589 filed Apr. 10, 2007, the disclosure of which is hereby incorporated herein by reference.

FIELD OF THE INVENTION

The example embodiments disclosed herein relate to systems and/or methods for visualizing treatment data collected while a patient is treated for sleep-disordered breathing. More particularly, the example embodiments disclosed herein relate to systems and/or methods for visualizing treatment data collected while a patient is treated for sleep-disordered breathing and may include a base pressure, pressure responses to one or more sleep-related triggering events (e.g., apnea, hypopnea, flattening, snore, etc.), and also indicate the type of triggering event corresponding to each particular pressure response.

BACKGROUND OF THE INVENTION

Obstructive Sleep Apnea (OSA) and other dangerous sleep-disordered breathing (SDB) conditions affect millions worldwide. Numerous techniques have emerged for the treating SDB, including, for example, the use of Continuous Positive Airway Pressure (CPAP) devices, which continuously provide pressurized air or other breathable gas to the entrance of a patient's airways via a patient interface (e.g., a mask) at a pressure elevated above atmospheric pressure, typically in the range 3-20 cmH$_2$O, or higher. SDB might also be treated with a high flow treatment device via a nasal cannula or other nasal patient interface such that the high flow treatment device generates warm humidified breathable gas or air at flows that may range from about 1 to 60 liters per minute. Typically, patients suspected of suffering from SDB register with a certified sleep laboratory where sleep technicians fit patients with numerous data collectors (e.g., polysomnography) and monitor their sleep activity over a given period. After the patient is diagnosed, a treatment regimen usually is developed, identifying both a treatment apparatus (or treatment apparatuses) and program of use for the treatment apparatus(es).

FIG. 1 is a partial schematic view of a typical positive airway pressure (PAP) device. An impeller 1 is powered by an electric motor 2 using a servo 3 under the direction of a microprocessor-based controller 4 (sometimes called a processor). The supply of breathable gas is carried to the mask 5 through a flexible conduit 6. The apparatus has various switches 7, displays 8, and a number of transducers. The transducers may monitor a number of processes, such as, for example volumetric flow rate 10 (e.g., at a predetermined point in the flow path), pressure 11 (e.g., at a predetermined point downstream of the flow generator outlet or at the mask), snore 12, flow generator rotational speed 13, and/or motor parameters 14.

Some treatment devices currently implement a series of algorithms that assess different respiratory parameters (such as, for example, snore, flattening, apnea, etc.) and then adjust the delivered pressure according to predetermined conditions. Only the total delivered pressure is reported to the clinician and/or patient. Certain other current products have been used to report a number for each pressure aspect. U.S. Pat. Nos. 5,245,995, 6,398739, 6,635,021, 6,770,037, 7,004,908, 7,141,021 each relate to automatically adjusting PAP devices, and the entire contents of each hereby are incorporated herein by reference.

It is advantageous to track the treatment pressure over time, for example, to aid in diagnosis and treatment. Unfortunately, however, such techniques either do not present the full range of data or present some or all of the data in a fashion that results in a diminished utility. For example, although some conventional devices present statistical reports, the reports may be difficult to understand and difficult to visualize when trying to obtain a more complete picture of a particular treatment under review and the events that led to the specific treatment being taken by an automatically adjusting PAP device. At least some of the information typically is in the PAP device, but it is difficult or impossible to access, or is simply not organized or presentable to the patient and/or clinician in a way that is helpful for diagnosis and/or treatment.

Thus, it will be appreciated that there is a need in the art for improved techniques for understanding how the delivered pressure is calculated.

SUMMARY OF THE INVENTION

One aspect of certain example embodiments relates to techniques for visualizing treatment data collected while a patient is treated for sleep-disordered breathing.

Another aspect of certain example embodiments relates to techniques for visualizing the pressure responses of a PAP device to one or more sleep-related triggering events (e.g., apnea, hypopnea, flattening, snore, etc.) over time.

In certain example embodiments, a method of visualizing patient treatment data collected while a patient suffering from sleep-disordered breathing is treated is provided. Pressure settings for patient treatment may be initialized. A supply of pressurized breathable gas may be provided to the patient based at least in part on the pressure settings. A triggering event may be detected. When a triggering event is detected, the pressure settings may be adjusted based at least in part on the triggering event type. A visual depiction of provided pressures over time may be created.

According to certain other example embodiments, a PAP device for treating a patient suffering from sleep-disordered breathing is provided. A processor may be set or programmed to generate a signal indicative of a triggering event. A flow generator may be configured to provide a supply of pressurized breathable gas to the patient based at least in part on the signal. Recording programmed logic circuitry may be provided to record in a data log pressures provided during patient treatment and triggering events occurring during patient treatment. Visualizing programmed logic circuitry in communication with the PAP device may be configured to read the data log and generate a visual depiction of provided pressures over time.

According to still other example embodiments, a visualization of treatment data collected while a patient is treated for sleep-disordered breathing is provided. The visualization may include a base pressure provided to the patient by a PAP device and may indicate at least one pressure response of the PAP device in response to one or more triggering events.

According to certain other example embodiments, a method of analyzing a treatment applied to a patient for sleep-disordered breathing is provided. A visual display may be generated based on pressure data from a PAP device in which each change in treatment pressure over time is visually associated with a sleep-related triggering event.

Certain example embodiments may produce a technical effect including, for example, the visualization of treatment data collected while a patient is treated for sleep-disordered breathing that include a base pressure, pressure responses to one or more sleep-related triggering events (e.g., apnea, hypopnea, flattening, snore, etc.), while also optionally indicating the type of triggering event corresponding to each particular pressure response. In other words, a technical effect of displaying a total pressure delivered to a patient while also indicating the sleep-related triggering events that caused pressure responses contributing to the total pressure delivered.

Various aspects of certain example embodiments may be combined with aspects of certain other example embodiments to realize yet further embodiments.

Other features of the invention will be apparent from the information contained in the following detailed description.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
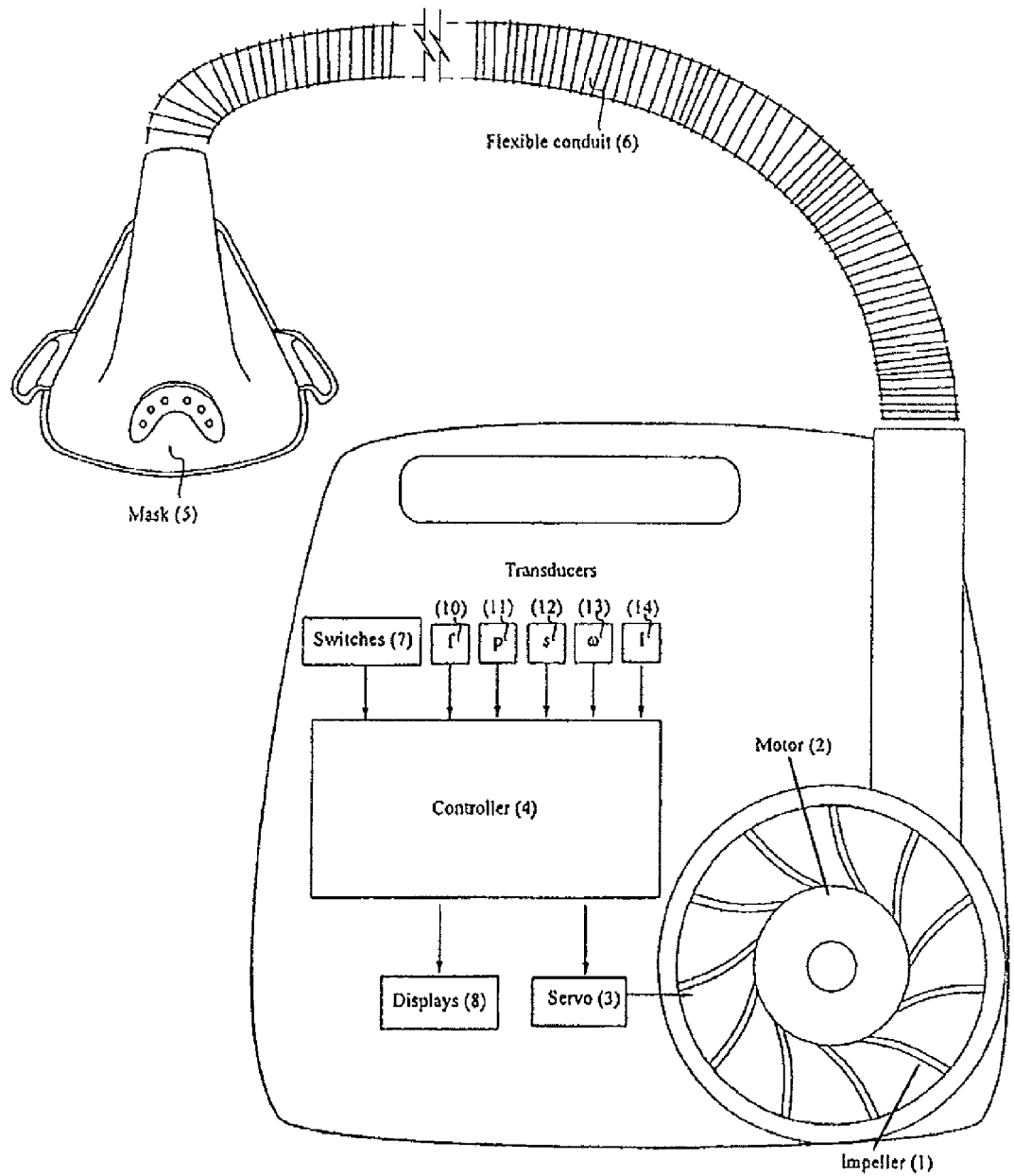
FIG. 1 is a partial schematic view of a typical PAP device.
Figure 2:
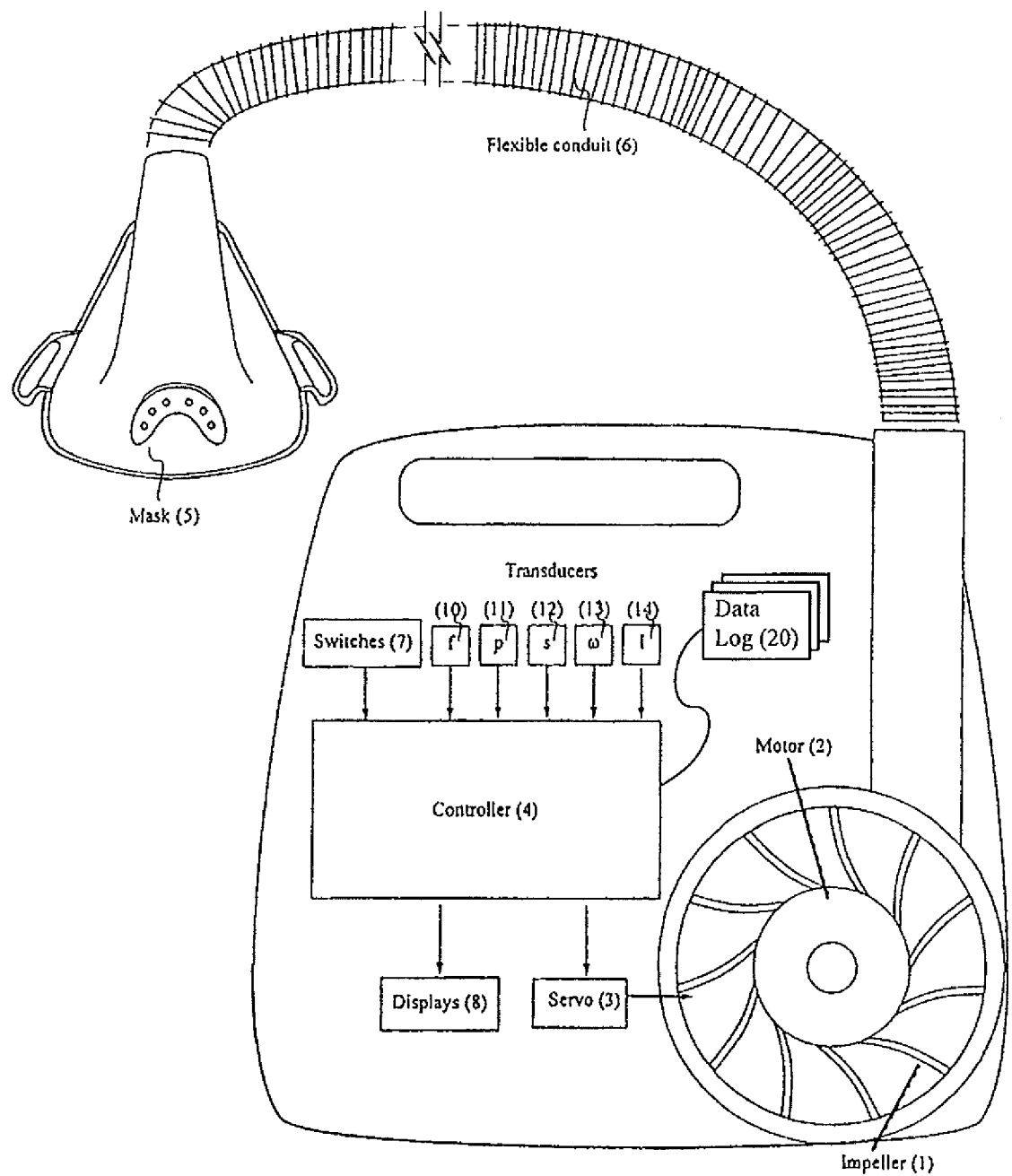
FIG. 2 is a partial schematic view of a PAP device in accordance with an example embodiment.

Referring now more particularly to the drawings, FIG. 2 is a partial schematic view of a PAP device in accordance with an example embodiment. FIG. 2 is similar to FIG. 1, except that the PAP device of FIG. 2 includes recording programmed logic circuitry for recording information to a data log 20. For example, the controller 4 (sometimes called the processor) may be configured to record pressures over time based on readings from the pressure transducer 11. In addition to storing the pressures, the controller 4 also may store events that cause changes in pressures and/or the times at which such events occur.

Various events may trigger a change in pressure. Such sleep-related triggering events may include, for example, an apnea, hypopnea, patient snore, flattening, etc. Pressure also may be adjusted over the course of a night's treatment, for example, to acclimate the patient to the pressure (e.g., the pressure may be low when the patient is falling asleep and gradually increase or ramp up until the patient is in a deep sleep). Similarly, pressures may be changed during various sleep stages (e.g., different pressures may be provided during waking or drowsiness, light sleep, NREM sleep, REM sleep, etc.).

Certain devices (e.g., Bilevel devices) also provide different pressures during patient inhalation and exhalation. In such cases, in certain example embodiments, pressures may be logged accordingly for both inhalation and exhalation over a patient breath (as sometimes referred to as IPAP and EPAP pressures). In certain other example embodiments, the different pressures may be aggregated in some way. For example, the average pressure delivered may be calculated and recorded. The controller 4 may be able to process the data stored in the data log 20. For example, the controller 4 may graphically present data corresponding to the pressures delivered over a patient's sleep.

One benefit to graphically presenting this data is that it shows why a PAP device is responding in a particular way. This information is advantageous for clinicians, especially during titration, to determine the appropriate PAP pressure. The information also may be useful for clinicians routinely assessing a patients condition. The individual's triggers can be seen, presenting a more intuitive picture of the overall treatment and enabling the therapy pressure to be determined more appropriately. For example, central apneas can be ignored in terms of setting the therapy pressure. In addition, clinicians can more effectively and more independently determine whether the device is effective (e.g., in reducing snore, apnea, hypopnet, etc.). The visual presentation also provides verification for clinicians that the systems are working, making the process more transparent and allowing clinicians to focus on aspects of physiology that were not previously available. For example, this also may be helpful when creating future treatment regimens for the patient.

Various data may be combined and presented on a single graph. For example, data may be compressed and a graph may be presented to include apnea pressure along with snore pressure, flattening pressure, and/or base pressure. As noted above, these techniques also may be applicable to Bilevel device titration, where the EPAP and/or the IPAP may be determined and the device, for example, may set the IPAP where no flattening occurs and the EPAP where no apneas occur.

Figure 3:
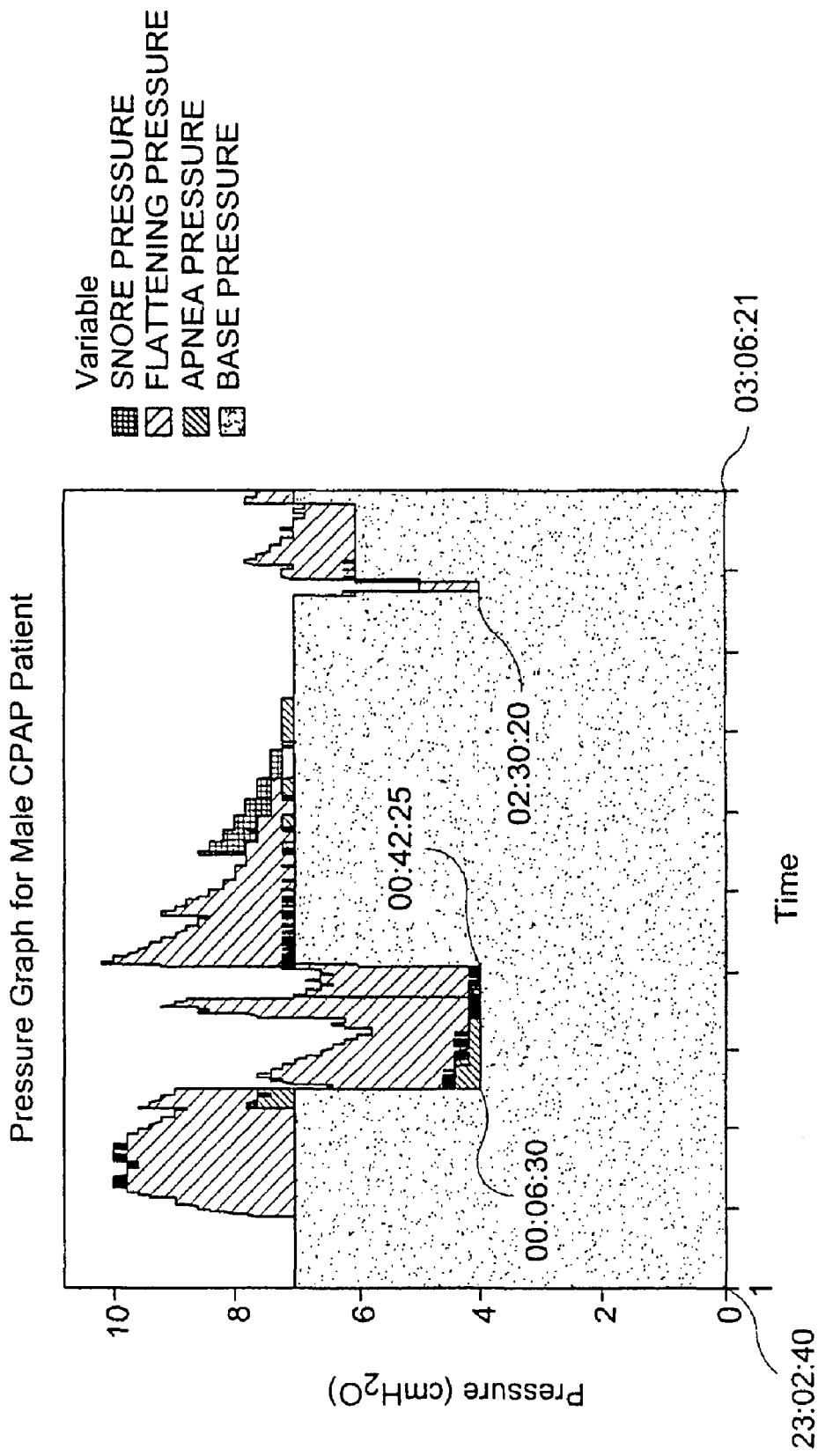
FIG. 3 is an illustrative pressure vs. time graph for a male patient receiving CPAP therapy, the graph being created in accordance with an example embodiment.

FIG. 3 is an illustrative pressure vs. time graph for a male patient receiving CPAP therapy, the graph being created in accordance with an example embodiment. This graph shows an artificial reduction in the base pressure to induce changes in pressure as a result of apneas. In other words, it is showing what occurred when the base minimum pressure was artificially and deliberately reduced by a clinician to induce an apnea during an overnight titration. In the example shown in FIG. 3, the pressure is set to a base pressure (about 7 cmH$_2$O) at the beginning of treatment (which is time stamped at 23:02:40) and increased in response to flattening. An apnea event occurs, at the artificial reduction in the base minimum pressure just a few minutes after midnight (at 00:06:30). When, for example, the apnea is normalized, the base pressure again was increased. Snore is detected, and the change in pressure is noted accordingly. Other events are recorded during the course of the patient's sleep.

Figure 4:
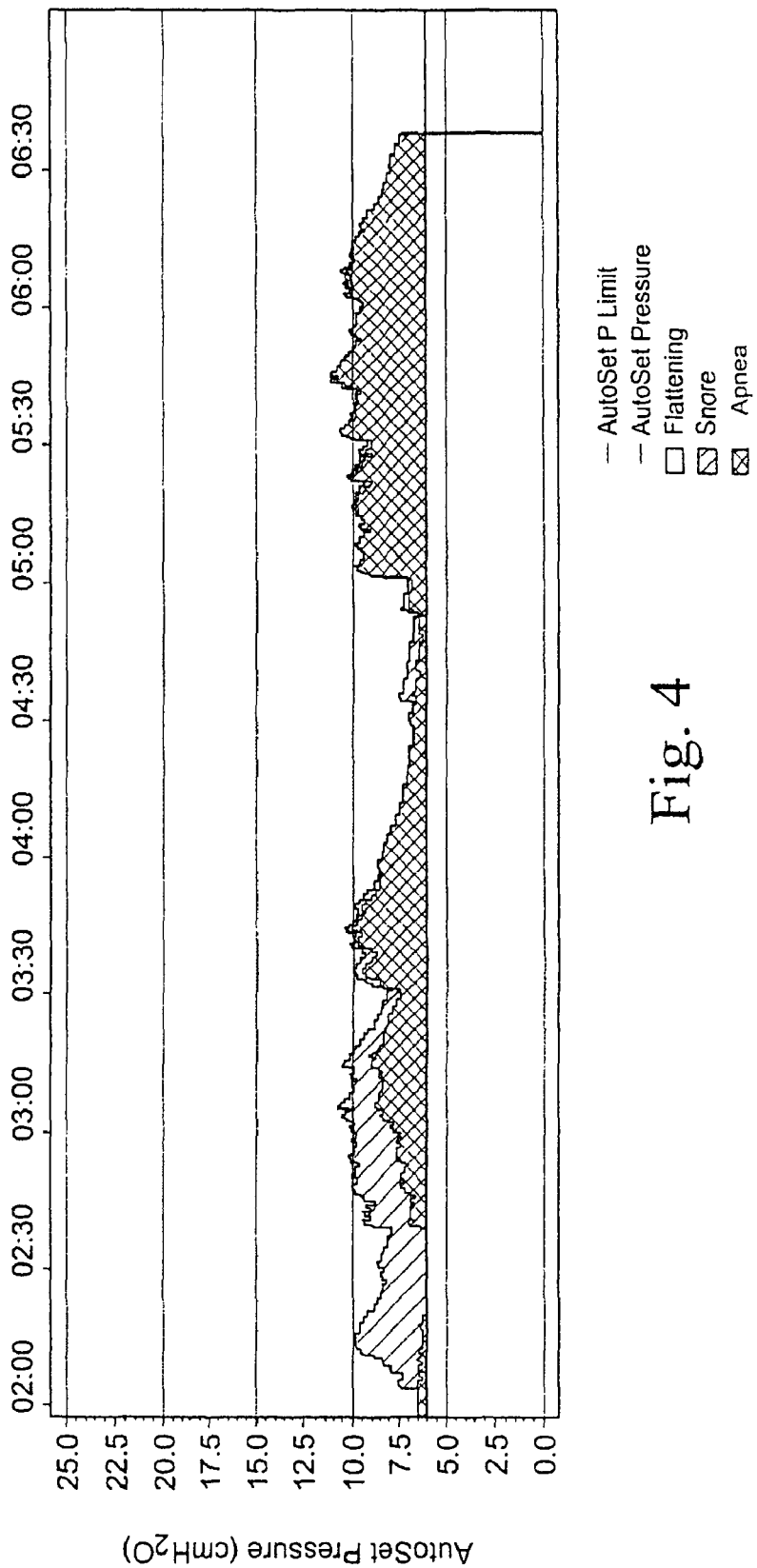
FIG. 4 is an illustrative pressure vs. time graph for a patient receiving AutoSet treatment, the graph being created in accordance with an example embodiment; and, FIG. 5 is a flowchart showing an illustrative process for visualizing treatment data in accordance with an example embodiment.

FIG. 4 is an illustrative pressure vs. time graph for a patient receiving AutoSet treatment, the graph being created in accordance with an example embodiment. Not all of the triggering events need to be recorded and displayed. For example, in FIG. 4, only patient flattening, snore, and apnea pressures are shown, along with the AutoSet pressure limit. In certain example embodiments, the controller 4 may be instructed to record only certain events (e.g., total delivered pressure, snore, patient flattening, etc.), whereas in certain other example embodiments it may be possible to record all and later filter out undesired information (e.g., apnea, hypopnea, etc.). For example, a user interface may be provided for selectively choosing the types of triggering events (e.g., all, some or one) for display so that the pressure settings or pressure response particularly associated with the selected types of events will be displayed in a particular graph to the extent that they have occurred within a chosen or predetermined time frame of the graph.

The data log 20 information and/or processed information may be stored to a computer-readable storage medium that may be removable from the PAP device. In certain example embodiments, the data log 20 information and/or processed information may be transmitted (e.g., wirelessly transmitted) from the PAP device to a remote location. Similarly, the data in raw and/or processed form may be displayable on a display connected to the device or may be retrieved and displayed on a separate display device or even on a display of the PAP device. The display may be substantially continuously updated (e.g., in real-time, on-the-fly, etc.), updated at predetermined time intervals (e.g., every 15 minutes, every half hour, every hour, etc.), with each triggering event, and/or the data may be stored and processed at a later time. The visualization may also, for example, be initiated and displayed after a treatment session to show data from one or more prior sessions.

Additional statistical data may be provided for the same information. Of course, it will be appreciated that presenting such statistical information alone may be of reduced value for the clinician because, as noted above, presenting data in a visual manner has led to one or more of the above-noted advantages.

Figure 5:
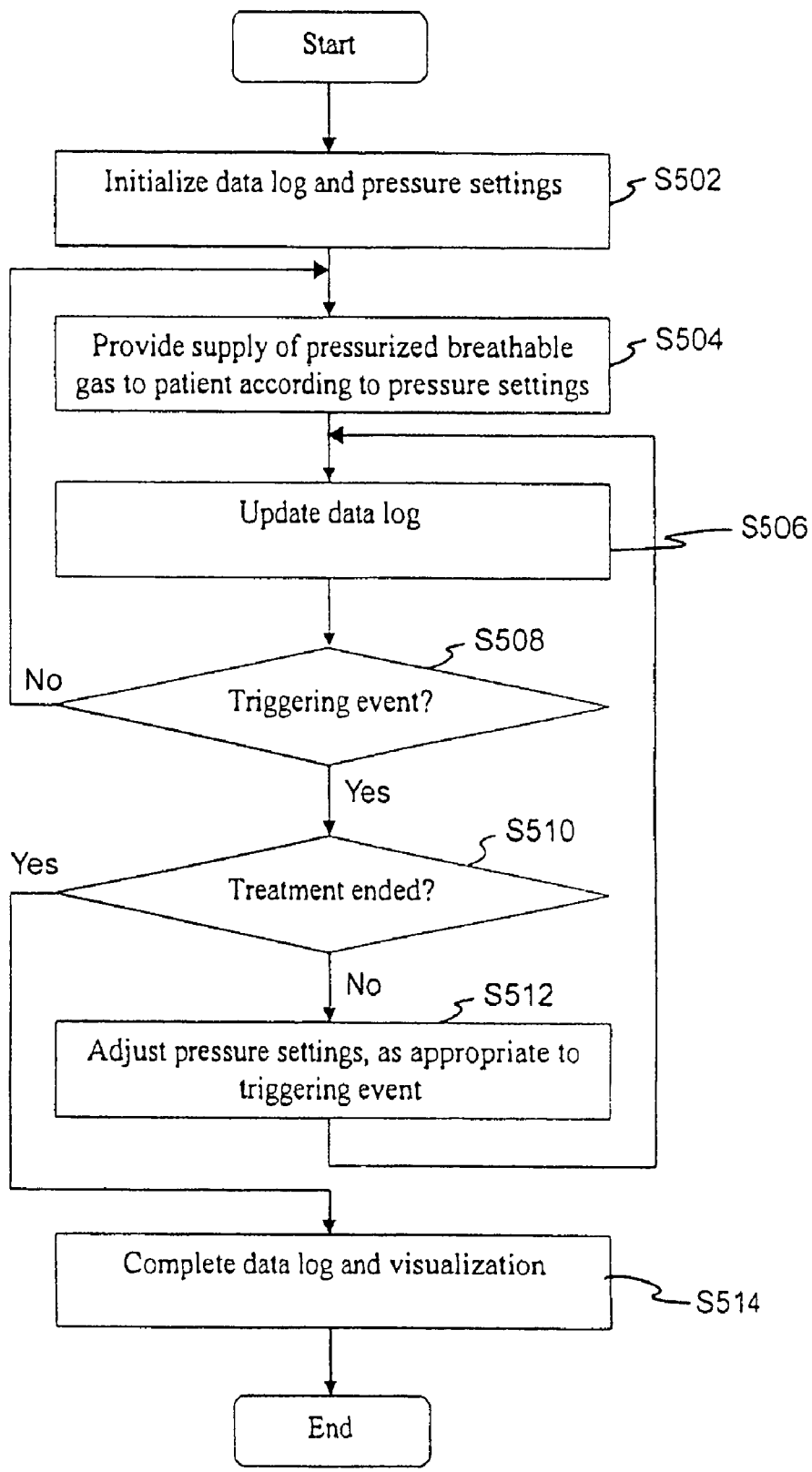

FIG. 5 is a flowchart showing an illustrative process for visualizing treatment data in accordance with an example embodiment. In FIG. 5, the data log and pressure settings are initialized in step S502. Then, in step S504, a supply of pressured breathable gas is provided to the patient according to the pressure settings. The data log is updated in step S506, and it includes at least the pressure settings and the time. As noted above, the data log may include the pressure, time, sleep event/trigger (if applicable), etc. If no triggering event is detected in step S508, then the process continues by providing a supply of pressurized breathable gas. However, if there is a triggering event and the treatment has not ended in step S510, the pressure settings are adjusted as appropriate to the triggering event in step S512. The process returns to step S506, where the data log is updated, for example, to include the new pressure settings, the time, the event that caused the change, etc. If, however, the treatment is over or a predetermined time period has elapsed, the data log is completed and the visualization is created and/or displayed in step S514.

Of course, it will be appreciated that, as noted above, the visualization may be displayed during the course of treatment. In such a case, the data log may be processed in real-time, in batch, etc. to cause a more frequent update of data.

Although certain example embodiments have been described as presenting visualizations of data, they are not limited to any particular form of visualization. For example, the data may be presented as an area graph as shown in FIGS. 3 and 4. Data also may be displayed as a line chart, bar graph, or other format. In general, a visualization may include a base pressure and pressure responses to triggering events over time. Such visualizations optionally may indicate the type of triggering event causing each particular pressure response.

The visualizations also may be more interactive than a mere area graph. For example, in certain example embodiments, a clinician or other user may position a mouse or cursor over a particular area or region to obtain more detailed information about the treatment at that point (e.g., the exact time of the event, the cause of the event, statistics about the event such as, for example, its length, whether it repeated, how often it repeated, etc.). A clinician or other user similarly may enlarge, refocus, move, filter, or perform other manipulations to the visualization, for example, to increase its usability and/or explanatory power.

Also, although certain processes have been described as being undertaken by the controller 4, the present invention is not so limited. For example, the data gathering, processing, visualization, and other features may be taken by the controller 4 alone or in combination with any other suitable programmed logic circuitry, on or off of the PAP device. For example, the data log 20 may be stored to a removable computer-readable storage medium for later processing by another computer. As alluded to above, visualizing programmed logic circuitry for creating a visualization of the data (e.g., a graph) may be located on the PAP device, on a separate computer system, etc. Also, as used herein, the term programmed logic circuitry is intended to encompass any suitable combination of hardware, software, firmware, or the like. By way of further example, the controller 4 may optionally be coupled with or include a graphics controller (not shown) to assist with the graphical display of information on a display 8 of the device and/or to provide an adapter for coupling an external display for presenting the graphic information.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. For example, the information displayed on or from a high flow treatment device may graphically present setting information in terms of base flow and flow response to triggering events determined by the high flow treatment device such as by showing liters/minute of the flow settings or pressure settings. Also, the various embodiments described above may be implemented in conjunction with other embodiments, e.g., aspects of one embodiment may be combined with aspects of another embodiment to realize yet other embodiments. By way of further example, the visualization created and displayed may combine live or real time data and historic data onto a common visualization for comparison of present and/or past events and/or pressure from one or more treatment sessions (e.g. a nights treatment). For example, the visualization may compare or display pressures from different sessions such as different nights, different weeks or it may compare pressures from a current session and one or more prior sessions, etc.

In addition, while the invention has particular application to patients who suffer from OSA, it is to be appreciated that patients who suffer from other illnesses (e.g., ventilatory insufficiency or failure, congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A method of visualizing patient treatment data collected while a patient suffering from sleep-disordered breathing is treated, the method comprising:
   initializing pressure settings for patient treatment;
   providing a supply of pressurized breathable gas to the patient based at least in part on the pressure settings;
   detecting sleep disorder breathing events;
   when a sleep disorder breathing event is detected, adjusting the pressure settings based at least in part on the sleep disorder breathing event type to supply gas at an adjusted pressure; and creating a visual depiction of provided pressures over time, wherein the supply of pressurized breathable gas is provided at a base pressure, and wherein creating a visual depiction comprises creating a visual depiction of the base pressure and adjusted pressure to indicate a relationship between a portion of the adjusted pressure and each sleep disorder breathing event type.

2. The method of claim 1 wherein creating a visual depiction of provided pressures over time occurs as a real time display of provided pressures during present treatment.

3. The method of claim 1 wherein the visual depiction of provided pressures includes data from two or more treatment sessions.

4. The method of claim 1, wherein the sleep disorder breathing event includes apnea, hypopnea, flattening, and/or snore.

5. The method of claim 4, wherein the visual depiction is an area graph.

6. The method of claim 5, wherein the visual depiction includes pressures provided to the patient for each sleep disorder breathing event.

7. The method of claim 6, wherein the visual depiction indicates a sleep disorder breathing event type associated with the provided pressures.

8. The method of claim 7, further comprising recording to a data log sleep disorder breathing event information and/or the pressure settings.

9. The method of claim 8, further comprising updating the visual depiction at a predetermined interval and/or when a sleep disorder breathing event is detected.

10. The method of claim 9, wherein Bilevel pressures are provided.

11. The method of claim 10, further comprising:
aggregating the provided Bilevel pressures over a breath; and
basing the visual depiction based on the aggregated Bilevel pressures.

12. The method of claim 1 wherein the visual depiction includes information from multiple sleep disorder breathing events.

13. A PAP device for treating a patient suffering from sleep-disordered breathing, comprising:
a processor set or programmed to generate a signal indicative of a sleep disorder breathing event;
a flow generator configured to provide a supply of pressurized breathable gas to the patient based at least in part on the signal;
recording programmed logic circuitry to record in a data log pressures provided during patient treatment and sleep disorder breathing events occurring during patient treatment; and,
visualizing programmed logic circuitry in communication with the PAP device configured to read the data log and generate a visual depiction of provided pressures over time, the visual depiction indicating a relationship between a portion of provided pressures and each sleep disorder breathing event.

14. The PAP device of claim 13, wherein the sleep disorder breathing event includes apnea, hypopnea, flattening, and/or snore.

15. The PAP device of claim 13, wherein the visual depiction is an area graph.

16. The PAP device of claim 13, wherein the visual depiction includes pressures provided to the patient for each sleep disorder breathing event.

17. The PAP device of claim 13, wherein the visual depiction indicates a sleep disorder breathing event type associated with the provided pressures.

18. The PAP device of claim 13, wherein the visualizing programmed logic circuitry is capable of displaying the visualization on a display.

19. The PAP device of claim 18, wherein the visualizing programmed logic circuitry updates the display at a predetermined interval and/or when a sleep disorder breathing event is detected.

20. The PAP device of claim 19, wherein the flow generator is configured to provide Bilevel pressures.

21. The PAP device of claim 20, wherein the recording programmed logic circuitry is configured to store aggregated Bilevel pressures.

22. The PAP device of claim 21, wherein the PAP device is an AutoSet device.

23. The PAP device of claim 22, wherein the visualizing programmed logic circuitry is located on a device separate from the PAP device.

24. The PAP device of claim 23, further comprising:
a mask for the patient, and
a flexible tube connecting the mask and the flow generator.

25. The PAP device of claim 24, wherein the flow generator is configured to provide the breathable gas at a pressure of about 3-20 cmH2O.

26. A visualization of treatment data collected while a patient is treated for sleep-disordered breathing, comprising:
a base pressure provided to the patient by a PAP device;
at least one pressure response of the PAP device in response to one or more sleep disorder breathing events; and
a visualization of the relationship between the at least one pressure response and each sleep disorder breathing event.

27. The visualization of claim 26, further comprising an indication of the type of sleep disorder breathing event associated with each said pressure response.

28. The visualization of claim 27, wherein the PAP device is an AutoSet device.

29. The visualization of claim 27, wherein the PAP device is a Bilevel device.

30. The visualization of claim 29, wherein each pressure included in the visualization is an aggregate of inhalation and exhalation pressures taken over a breath.

31. The visualization of claim 30, wherein a device on which is the visualization is displayed is configured to receive user input and adjust the visualization in response thereto.

32. A method of analyzing a treatment applied to a patient for sleep-disordered breathing, the method comprising generating a visual display based on pressure data from a PAP device in which each change in treatment pressure over time is visually associated with a sleep-related sleep disorder breathing event.

33. The method of claim 32, further comprising isolating, for each sleep disorder breathing event, an associated pressure contribution.

34. The method of claim 32, further comprising determining a future treatment pressure for a future treatment of the patient.

35. The method of claim 32, further comprising determining whether the treatment is effective.

36. The method of claim 35, further comprising determining whether the treatment is effective in reducing patient snore, apnea, and/or hypopnea.

37. The method of claim 36, further comprising disregarding at least some of the sleep disorder breathing events.

38. The method of claim 37, further comprising verifying whether the PAP device is functioning properly.

39. A high flow treatment device for treating a patient suffering from sleep-disordered breathing comprising:
- a processor with processor control instructions to generate a signal indicative of a sleep disorder breathing event;
- a flow generator to provide a response flow of breathable gas to the patient based at least in part on the signal;
- recording programmed logic circuitry to record in a data log data indicative of flows or pressures provided during patient treatment and of sleep disorder breathing events occurring during patient treatment; and
- visualizing programmed logic circuitry in communication with the high flow treatment device configured to read the data log and generate a visual depiction of flow generator responses associated with particular sleep disorder breathing events over time, the visual depiction indicating a relationship between a portion of the flow generator response and each sleep disorder breathing event.

* * * * *

UNITED STATES PATENT AND TRADEMARK OFFICE
CERTIFICATE OF CORRECTION

| | | |
|---|---|---|
| PATENT NO. | : 8,276,585 B2 | Page 1 of 1 |
| APPLICATION NO. | : 11/998852 | |
| DATED | : October 2, 2012 | |
| INVENTOR(S) | : Mark David Buckley and Glenn Richards | |

It is certified that error appears in the above-identified patent and that said Letters Patent is hereby corrected as shown below:

In the Specifications

Column 1, line 32, "for the treat-" should read -- for treat- --
Column 4, line 14, "patients" should read -- patient's --
Column 4, line 15, "seen," should read -- seen --

In the Claims

Column 8, line 27, "H2O" should read -- $H_2O$ --
Column 8, line 47, "which is the" should read -- which the --

Signed and Sealed this
Sixth Day of May, 2014

Michelle K. Lee
*Deputy Director of the United States Patent and Trademark Office*